United States Patent [19]

Ichikawa et al.

[11] 4,229,471
[45] Oct. 21, 1980

[54] N-(2-ETHYLHEXYL)-CROTONAMIDES

[75] Inventors: Atsushi Ichikawa, Takatsuki; Kenkichi Tomita, Kyoto; Taku Horiuchi, Ninomiya; Shin-ichi Suzuki, Shizuoka; Akira Sakuma, Kamakura, all of Japan

[73] Assignee: The Lion Dentifrice Co., Ltd., Tokyo, Japan

[21] Appl. No.: 60,815

[22] Filed: Jul. 25, 1979

[30] Foreign Application Priority Data

Aug. 11, 1978 [JP] Japan .................................. 53-97889

[51] Int. Cl.² ...................... C07C 103/56; A61K 31/16
[52] U.S. Cl. ................................. 424/320; 260/561 N
[58] Field of Search .................... 260/561 N; 424/320

[56] References Cited

U.S. PATENT DOCUMENTS 2,529,838  11/1950  Erickson .......................... 260/561 N

FOREIGN PATENT DOCUMENTS 2522474 12/1975 Fed. Rep. of Germany ...... 260/561 N
2753792  6/1978 Fed. Rep. of Germany ...... 260/561 N

*Primary Examiner*—Arthur P. Demers
*Attorney, Agent, or Firm*—Birch, Stewart, Kolasch & Birch

[57] ABSTRACT

Novel compounds having the general formula:

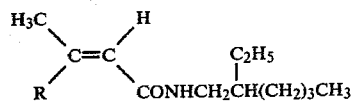

wherein R is selected from hydrogen and methyl, effectively inhibit the growth of cancerous cells. These compounds are useful as carcinostatic agents.

4 Claims, 5 Drawing Figures

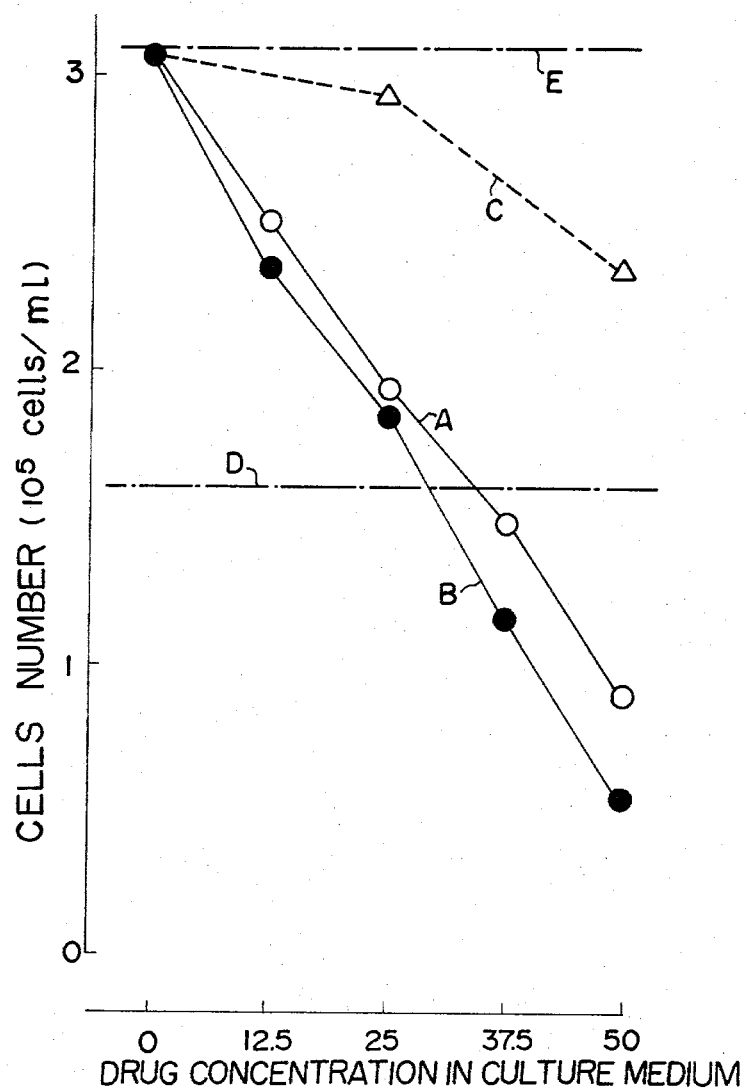

N-(2-ETHYLHEXYL)-CROTONAMIDES

BACKGROUND OF THE INVENTION

This invention relates to novel compounds having the general formula:

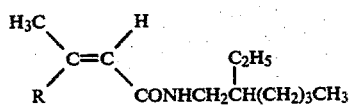

wherein R is hydrogen or methyl. More particularly, this invention relates to novel compounds of formula I which are effective in inhibiting the growth of cancerous cells and thus useful as a carcinostatic agent.

West German Offenlegungsschrift No. 2,522,474 discloses N-alkylacrylamides having the general formula:

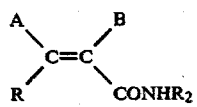

wherein R represents alkyl group; $R_2$ represents alkyl or substituted alkyl group having at least 4 carbon atoms; A and B represent alkyl group or hydrogen, respectively, or A and B form vinylene group or 6-membered carbocylic or heterocyclic ring. The compounds of formula II are used as agricultural agents or germicides. However, this Offenlegungsschrift neither specifically discloses the compounds of formula I nor indicates their carcinostatic activity.

The inventors have found that the compounds of formula I which can be prepared by reacting 2-ethylhexylamine with a lower alkyl ester or similar derivative of crotonic acid or β-methyl crotonic acid are novel and have higher carcinostatic activity than N-(2-ethylhexyl)-β-hydroxybutyramides which are known as effective carcinostatic agents (West German Offenlegungsschrift No. 2,753,792).

SUMMARY OF THE INVENTION

Therefore, an object of this invention is to provide a novel compound of formula I capable of effectively inhibiting the growth of cancerous cells and thus being useful as a carcinostatic agent.

Another object of the invention is to provide a carcinostatic pharmaceutical composition comprising an effective carcinostatic amount of a compound of formula I and a pharmaceutically acceptable carrier.

The above and other objects, features and advantages of the invention will become more apparent upon a reading of the following description.

BRIEF DESCRIPTION OF THE DRAWINGS

FIG. 5 is a graph showing the effect of drugs on the inhibition of the growth of cancerized mast cells (Mastocytoma P-815) during 20 hours of cultivation.

DETAILED DESCRIPTION OF THE INVENTION

The novel compounds of this invention are represented by the above general formula I. Specifically, this invention provides:

N-(2-ethylhexyl)-crotonamide represented by the chemical structure III,

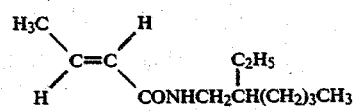

and

N-(2-ethylhexyl)-β-methylcrotonamide represented by the chemical structure IV.

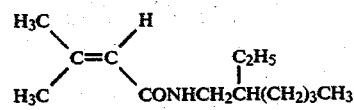

N-(2-ethylhexyl)-crotonamide is a colorless solid, having its melting point at 47°–48° C. N-(2-ethylhexyl)-β-crotonamide is an oily substance. These compounds are both insoluble in water but soluble in organic solvents such as acetone.

Figure 1:
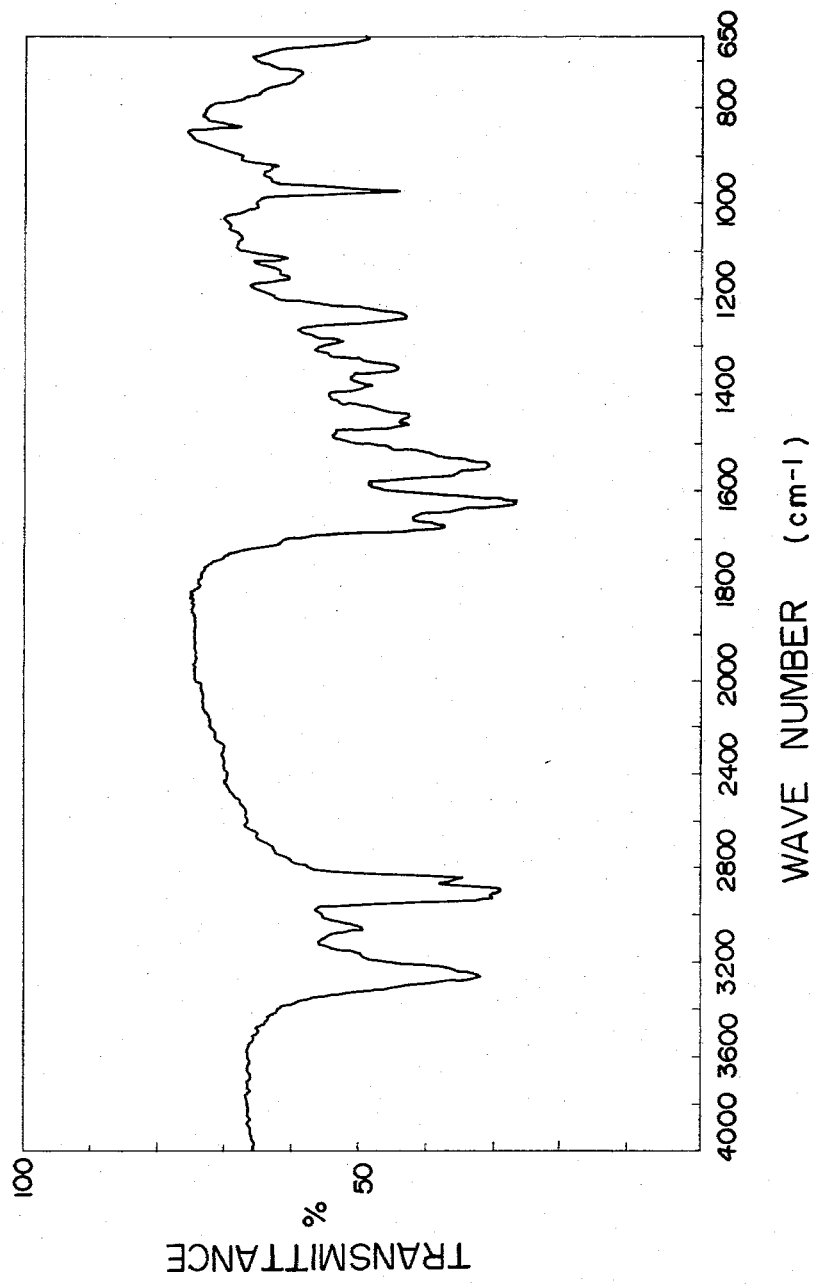
FIGS. 1 and 2 are the IR and NMR spectrum of the novel compound, N-(2-ethylhexyl)-crotonamide, respectively.
Figure 2:
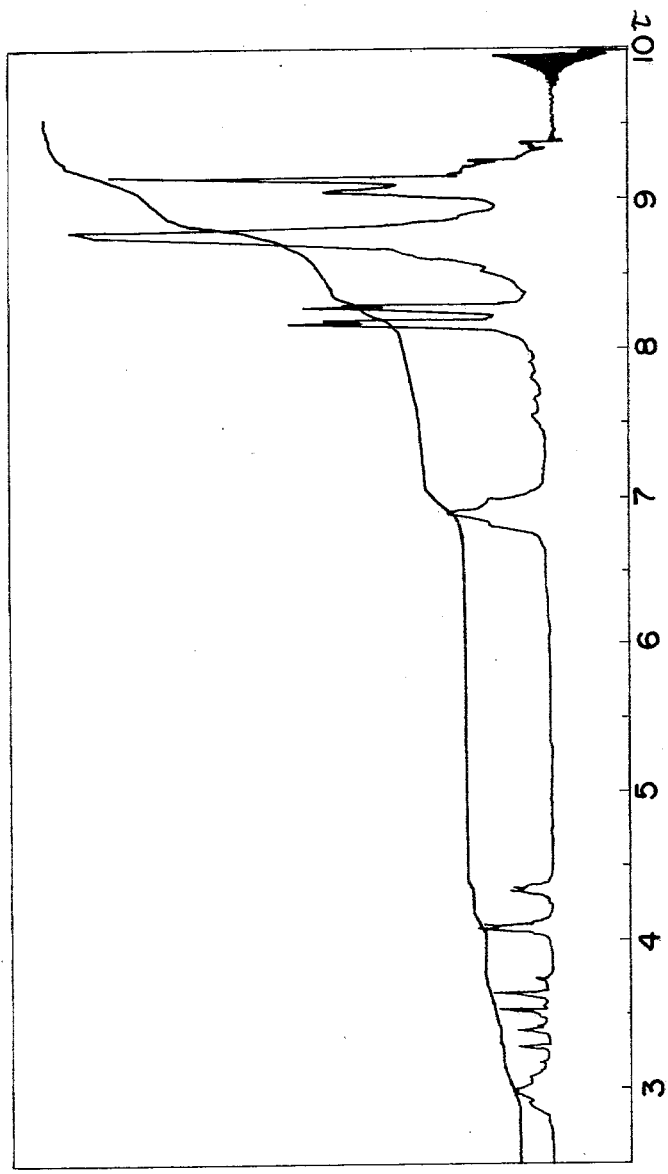
Figure 3:
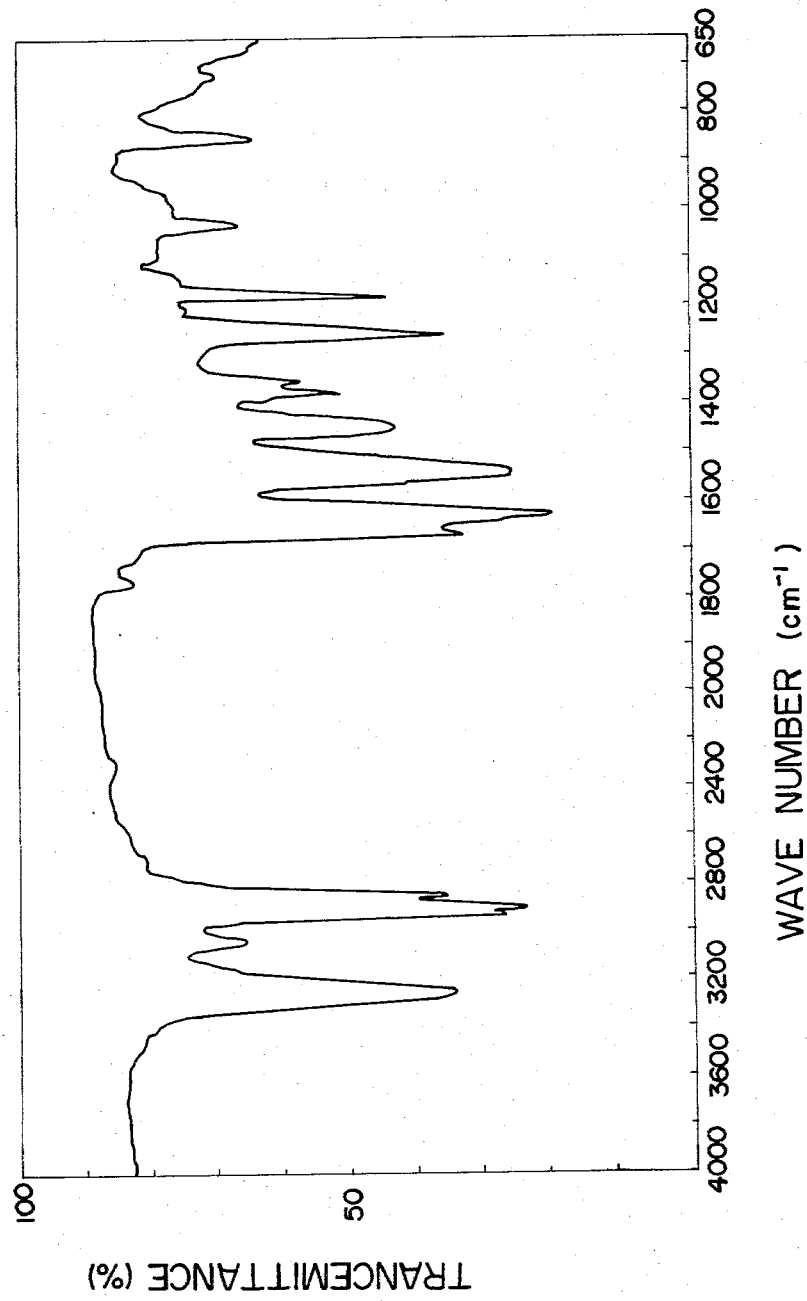
FIGS. 3 and 4 are the IR and NMR spectrum of the novel compound, N-(2-ethylhexyl)-beta-methyl-crotonamide, respectively.
Figure 4:
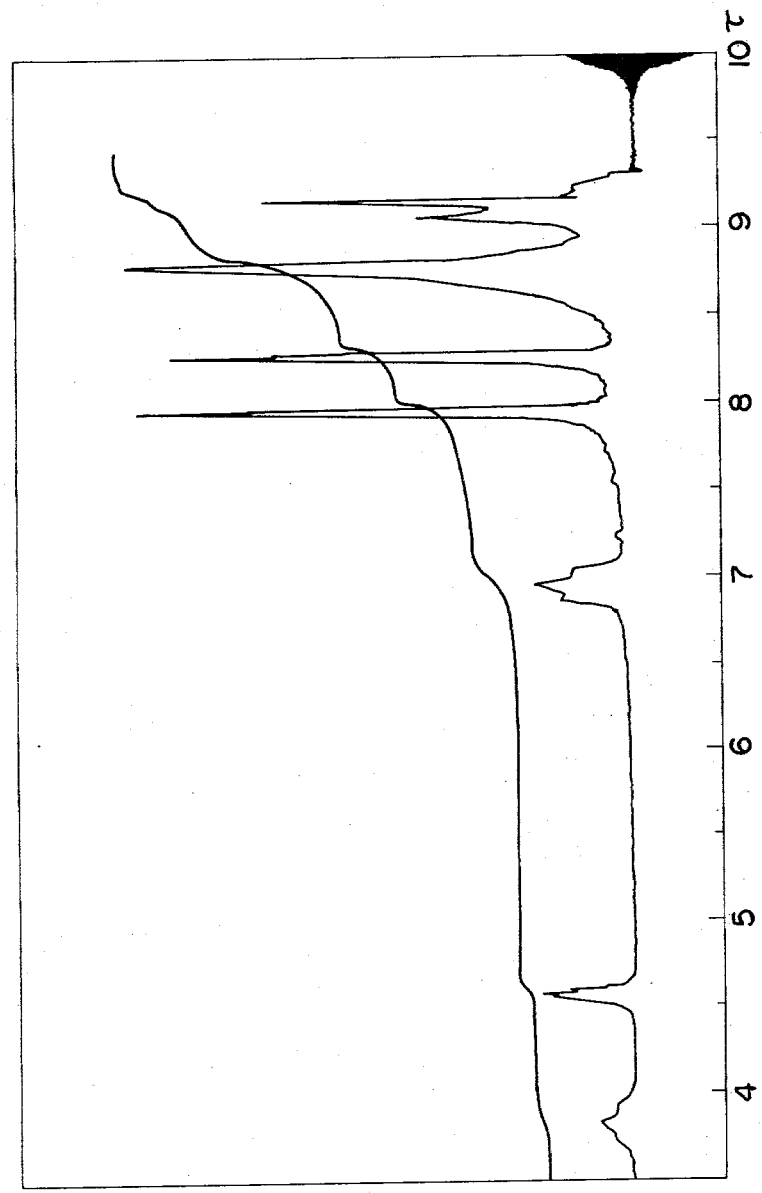

The IR and NMR spectrum of N-(2-ethylhexyl)-crotonamide are illustrated in FIGS. 1 and 2, respectively, and the IR and NMR spectrum of N-(2-ethylhexyl)-β-methylcrotonamide are illustrated in FIGS. 3 and 4, respectively.

The compounds of general formula I may be prepared according to the following reaction scheme, by reacting a lower alkyl ester (formula V), a halide (formula VI) or an anhydride (formula VII) of crotonic acid or β-methylcrotonic acid with 2-ethylhexylamine (formula VIII), or by using an N-(2-ethylhexyl)-β-hydroxybutyramide derivative (formula IX) as a starting material.

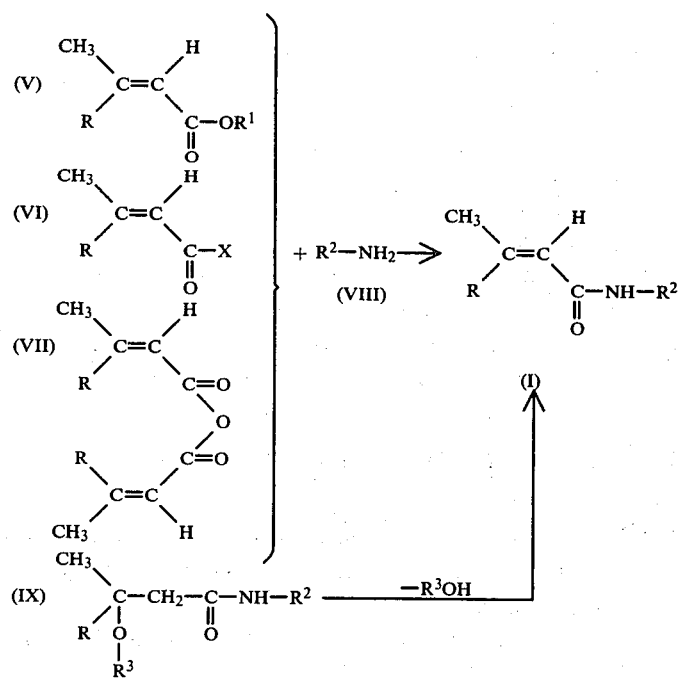

In the above formulae, R is hydrogen or methyl, $R^1$ is a lower alkyl group having 1 to 5 carbon atoms, $R^2$ is 2-ethylhexyl, $R^3$ is a residue of a monobasic carboxylic acid such as acetic acid, propionic acid, butyric acid or the like, or a dibasic carboxylic acid such as succinic acid, glutaric acid, alphaketoglutaric acid or the like, or a sodium or potassium salt thereof, and X is a halogen atom such as chlorine, bromine or the like.

The compounds of formula I have substantial carcinostatic activity. Specifically, the compounds are effective in inhibiting the division of cancerized mast cells such as Mastocytoma and DNA synthesis so that the compounds are valuable as carcinostatic agents.

The results of an acute toxicity test of these compounds are shown in Table 1.

TABLE 1

| Compound | Animal | Administration | $LD_{50}$ (mg/kg) |
| --- | --- | --- | --- |
| N-(2-ethylhexyl)-crotonamide | ICR male mouse | intraperitoneal | 540 |
| N-(2-ethylhexyl)-beta-methylcrotonamide | ICR male mouse | intraperitoneal | 1400 |

The compounds of formula I may be administered by any desired method, for example, by way of intravenous injection, subcutaneous injection, oral administration or rectal administration. In the form of a dosage unit, the compound may be administered once or more times a day at appropriate intervals, always depending on the administration route and other factors in accordance with the prescription. For both N-(2-ethylhexyl)-crotonamide and N-(2-ethylhexyl)-betamethylcrotonamide, the preferred daily dose for adults may be 50 to 2,000 mg in the case of oral administration and 20 to 500 mg in the case of injection.

The compounds of formula I may be worked up to various pharmaceutical forms of presentation such as tablets, pills, dragees, suppositories, capsules, suspensions and the like by any desired pharmaceutical preparation method. Since N-(2-ethylhexyl)-crotonamide is solid and N-(2-ethylhexyl)-β-methylcrotonamide is an oily substance at room temperature, the preparation method may depend on the state of the compound to be used. Tablets and capsules including hard and soft capsules for oral administration may be prepared in the form of dosage units by routine methods using pharmaceutically acceptable, non-toxic carriers. For example, a binder selected from acacia, gelatin, sorbitol, tragacanth, polyvinyl pyrrolidone and the like; a vehicle selected from lactose, sugar, corn starch, silicic acid anhydride, linoleic acid, propylene glycol and the like; a lubricant selected from magnesium stearate, talc and the like; a disintegrator such as potato starch; a wetting agent such as lecithin and other known carriers for medicaments are all suitable. The tablets and capsules may preferably be presented in the form readily absorbed from the gastro-intestinal tract. Liquid preparations for oral administration may be of suspension, emulsion, syrup or other forms. The preparations for mucosal application, particularly, suppositories, may use cacao butter, laurin, polyethylene glycol, glycerogelatium, sodium stearate and mixtures thereof as a base. The parenteral injections may also be prepared by conventional methods. Since the compounds of formula I are insoluble in water, they may be suspended or emulsified in water for injection. The suspending agent may be sorbitol syrup, methyl cellulose, gelatin, hydroxyethyl cellulose, aluminum stearate gel or the like. The emulsifier may be sorbitan monooleate, polyoxyethylene-hardened castor oil, lecithin or the like.

The invention will be further described in the following Examples which are not construed as limiting the invention.

First, the preparation of the compounds of formula I is illustrated.

EXAMPLE 1

Preparation of N-(2-ethylhexyl)-crotonamide

In a flask, 2.6 g (0.02 mol) of 2-ethylhexylamine and 1.0 g (0.01 mol) of methyl crotonate were admitted and refluxed for 6 hours. The reaction mixture was dissolved in n-hexane, washed first with diluted hydrochloric acid and then with 10% sodium hydroxide solution, and subsequently dried with sodium sulfate. The residue was recrystallized from n-hexane, obtaining 1.42 g of N-(2-ethylhexyl)-crotonamide (yield: 72.1%). Usual analysis was carried out to identify the compound. The results are shown below.

Crystal form: colorless needle
Melting point: 47°-48° C.
Elemental analysis: $C_{12}H_{23}NO$ (molecular weight 197.31)

|        | C      | H      | N     |
|--------|--------|--------|-------|
| Calcd. | 73.04% | 11.75% | 7.10% |
| Found  | 73.09% | 11.53% | 7.40% |

IR spectrum: FIG. 1 showed strong bands at 3020 (olefin), 1670 and 968 (trans olefin), and 1620 (=C=O) cm$^{-1}$.

NMR spectrum (CCl$_4$): FIG. 2 showed signals at $\tau$=4.22 (d, 1H, Ha) and 3.44 (m, 1H, Hb) Ja, b=16 cps, Internal standard=TMS

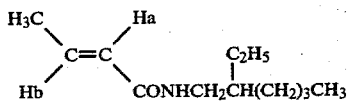

MS (m/e value): 197 (M+)

EXAMPLE 2

Preparation of N-(2-ethylhexyl)-crotonamide

In a flask, 10 g of N-(2-ethylhexyl)-$\beta$-hydroxybutyramide semisuccinate was admitted and heated at 170° C. for 4 hours. The reaction mixture was dissolved in n-hexane and the insolubles were removed by filtration. The filtrate was washed first with diluted hydrochloric acid and then with 10% sodium hydroxide solution, and subsequently dried with sodium sulfate. The residue was recrystallized from n-hexane, obtaining 5.01 g of N-(2-ethylhexyl)-crotonamide (yield: 80.1%). This compound showed substantially the same results as those in Example 1.

EXAMPLE 3

Preparation of N-(2-ethylhexyl)-$\beta$-methylcrotonamide

In 20 ml of n-hexane was dissolved 1.40 g (0.011 mol) of 2-ethylhexylamine. With stirring, 1.20 g (0.01 mol) of $\beta$-methylcrotonyl chloride was added to the solution. After reaction, the reaction mixture was washed first with diluted hydrochloric acid and then with 10% sodium hydroxide solution and subsequently dried with sodium sulfate. The solvent was distilled off and the residue was further distilled in vacuum. A fraction having a boiling point of 133°-134° C./1 mmHg was collected, obtaining 1.76 g of N-(2-ethylhexyl)-$\beta$-methylcrotonamide as an oil (yield: 82.3%). Usual analysis was carried out to identify the compound. The results are shown below.

Elemental analysis: $C_{13}H_{25}NO$ (molecular weight 211.35)

|        | C      | H      | N     |
|--------|--------|--------|-------|
| Calcd. | 73.88  | 11.92% | 6.63% |
| Found  | 73.89% | 11.93% | 6.59% |

IR spectrum: FIG. 3 showed strong bands at 3020 (olefin), 1180 (dimethyl), and 1630 (=C=O) cm$^{-1}$.

NMR spectrum (CCl$_4$): FIG. 4 showed signals at $\tau$=8.26 (S, 3H, CH$_3$ trans), 7.96 (S, 3H, CH$_3$ cis), and 4.58 (S broad, 1H, <C=CH) Internal standard=TMS MS (m/e value): 211 (M+).

Next, the compounds of formula I were tested for carcinostatic activity.

EXAMPLE 4

20 ml of a culture medium containing cancerized mast cells of a mouse (Mastocytoma P-815) at an inoculum cell concentration of 1.6×10$^5$ cells/ml in Fischer and Sartorelli's medium supplemented with 5% fetal calf serium were cultured in a 120 ml Erlenmeyer flask with or without drugs to be tested in an atmosphere of 5% CO$_2$ and 95% air at 37° C. for 20 hours in a humidified incubator. Drugs, N-(2-ethylhexyl)-crotonamide, N-(2-ethylhexyl)-$\beta$-methylcrotonamide or N-(2-ethylhexyl)-$\beta$-hydroxybutyramide were added in different amounts to the initial culture medium. No drug was added to a control solution. After cultivation, the number of cells was counted.

The results are shown in FIG. 5 wherein A corresponds to N-(2-ethylhexyl)-crotonamide, B corresponds to N-(2-ethylhexyl)-beta-methylcrotonamide, C corresponds to N-(2-ethylhexyl)-beta-hydroxybutyramide, D is the inoculum cell number, and E corresponds to the control. A, B, C and E are the cell numbers after 20 hour cultivation as described above.

As apparent from FIG. 5, N-(2-ethylhexyl)-crotonamide and N-(2-ethylhexyl)-$\beta$-methylcrotonamide are more effective than N-(2-ethylhexyl)-$\beta$-hydroxybutyramide in inhibiting the division and growth of cancerized mast cells under cultivation.

EXAMPLE 5

Mice of BDF$_1$ species (5 week old male, suppliers: Charles River and Shizuoka Laboratory Animal Center) were divided into four groups each containing three to six. Cancerized mast cells (Mastocytoma P-815) were implanted into the ascites of a mouse in an amount of 1×10$^6$ cells/mouse. From the next day, drug A: N-(2-ethylhexyl)-crotonamide,
B: N-(2-ethylhexyl)-beta-methylcrotonamide, or
C: N-(2-ethylhexyl)-beta-hydroxybutyramide was administered once a day by intra-peritoneal injection in an amount of 0.5 mg/mouse/day for 6 days, respectively. After 18 hours from the last administration, the mice were killed with ether for anesthesia. The entire ascitic cells were taken out with about 20 ml of phosphate buffered saline. Using the nigrosine staining method (0.01% nigrosine in Earl's balanced salt solution), the number of cells, particularly, live cells were counted by means of a Thomas leucocyte counting apparatus. The results are tabulated in Table 2.

For the above-described administration procedure was used 50 mg of the drug to which 25 mg of polyoxyethylene sorbitan monooleate (Tween 80) was added and the mixture was suspended in 5 ml of physiological salt solution and sterilized in an autoclave at 120° C. under 2 atm. for 15 minutes. The resulting sterile suspension was ready for administration.

TABLE 2

| Mouse species | Drug | Number*** of mice | Dose (mg/mouse/day) | Number of ascites cancer cells ($\times 10^8$/mouse) | Tumor** inhibition ratio (%) |
|---|---|---|---|---|---|
| Charles River BDF$_1$ | A | 4 | 0.5mg × 6 | 1.5 | 90.9 |
| | B | 4 | 0.5mg × 6 | 9.5 | 42.1 |
| | C | 4 | 0.5mg × 6 | 6.0 | 63.4 |
| | con-* trol | 6 | — | 16.4 | — |
| Shizuoka Laboratory Animal Center BDF$_1$ | A | 3 | 0.5mg × 6 | 1.2 | 87.6 |
| | B | 3 | 0.5mg × 6 | 4.0 | 58.8 |
| | C | 3 | 0.5mg × 6 | 6.7 | 30.9 |
| | con-* trol | 5 | — | 9.7 | — |

*0.5% Tween 80 of physiological salt solution was administered for the control group.
**Tumor inhibition ratio was calculated in terms of the following equation:

Tumor inhibition ratio (%) = $\frac{C - N}{C} \times 100$

C : number of ascites cancer cells in the control group
N : number of ascites cancer cells in the treated group
***In all the groups, the number of dead mice was 0 throughout the experiment.

EXAMPLE 6

Effects of drugs on $^3$H-TdR (tritium labelled thymidine) incorporation into DNA of cancerized mast cells were examined.

Cancerized mast cells (Mastocytoma P-815), $4.25 \times 10^6$ cells, were incubated for 15 minutes with or without each of drugs, A: (N-(2-ethylhexyl)-crotonamide), B: (N-(2-ethylhexyl)-β-methylcrotonamide) and C: (N-(2-ethylhexyl)-β-hydroxybutyramide) (each 100 μg and 500 μg) in 1 cc of Fischer culture medium. Thereafter, 0.1 μCi of $^3$H-TdR was added and incubation was proceeded for an additional 60 minutes. The cells were washed with PBS and the DNA was precipitated with 5% (W/V) trichloroacetic acid. Precipitates were counted in a liquid Scintillation Spectrometer. The results are shown in Table 3.

TABLE 3

| Drug | Dose (μg) | DNA synthesis cpm | inhibition* ratio (%) |
|---|---|---|---|
| A | 100 | 400 | 90.1 |
| | 500 | 75 | 98.1 |
| B | 100 | 200 | 95.1 |
| | 500 | 0 | 100.0 |
| C | 100 | 2205 | 45.6 |
| | 500 | 1200 | 70.4 |
| control | — | 4050 | — |

*Inhibition ratio was calculated in terms of the following equation:

Inhibition ratio (%) = $\frac{c - s}{c} \times 100$ c : amount of $^3$H—TdR incorporated in the control group (cpm)
s : amount of $^3$H—TdR incorporated in the treated group (cpm)

Table 3 shows that N-(2-ethylhexyl)-crotonamide and N-(2-ethylhexyl)-β-methylcrotonamide are effective in inhibiting DNA synthesis.

As apparent from the foregoing results, N-(2-ethylhexyl)-crotonamide and N-(2-ethylhexyl)-β-methylcrotonamide of the invention exhibit high carcinostatic activity showing their effective use as a carcinostatic agent.

The following are pharmaceutical Examples.

EXAMPLE 7

Capsule

N-(2-ethylhexyl)-crotonamide—200 g
corn starch—150 g
talc—80 g
magnesium stearate—30 g The above ingredients were fully admixed and passed through a screen of 60 mesh for particle size regulation. One thousand gelatin capsules were filled with this mixture. It will be effective to administer orally 1 to 3 capsules a day.

EXAMPLE 8

Capsule

N-(2-ethylhexyl)-beta-methylcrotonamide—180 g
silicic acid anhydride—60 g
magnesium stearate—5 g N-(2-ethylhexyl)-beta-methylcrotonamide was dissolved in acetone. Silicic acid anhydride was dispersed in this solution. After evaporation of acetone, the remainder was comminuted into a powder, which was passed through a screen of 60 mesh for particle size regulation. The resulting powder was admixed with magnesium stearate. One thousand gelatin capsules were filled with this powder mixture.

EXAMPLE 9

Tablet

N-(2-ethylhexyl)-crotonamide—200 g
lactose—50 g
corn starch—30 g
magnesium stearate—5 g The above ingredients were admixed and passed through a screen of 60 mesh for particle size regulation. This powder mixture was worked up into 1000 tablets by means of a tablet machine. It will be effective to administer orally 1 to 3 tablets a day.

EXAMPLE 10

Suppository cacao butter—1200 g
N-(2-ethylhexyl)-beta-methylcrotonamide—140 g

Cacao butter was melted by heating at 50° C. This molten cacao butter was homogeneously admixed with N-(2-ethylhexyl)-beta-methylcrotonamide. The resulting mixture was poured into a mold to form 1000 suppositories.

EXAMPLE 11

Parenteral solution

N-(2-ethylhexyl)-crotonamide—400 g
polyoxyethylene-hardened castor oil—500 g
distilled water for injection—10 liters The above ingredients were worked up into a parenteral solution according to the usual procedure. An ampoule was filled with 2 ml of the solution.

What is claimed is:

1. A compound represented by the formula:

wherein R is selected from the group consisting of hydrogen and methyl.

2. The compound N-(2-ethylhexyl)-crotonamide.

3. The compound N-(2-ethylhexyl)-β-methylcrotonamide.

4. A carcinostatic pharmaceutical composition comprising an effective carcinostatic amount of a compound according to claim 1, and a pharmaceutically acceptable carrier.

* * * * *